United States Patent
Rauch et al.

(10) Patent No.: US 12,220,416 B2
(45) Date of Patent: Feb. 11, 2025

(54) METHYLENE-TETRAHYDROFOLATE REDUCTASE ISOFORM-BASED BIOMARKER AND METHOD OF USE THEREOF

(71) Applicant: RUSH UNIVERSITY MEDICAL CENTER, Chicago, IL (US)

(72) Inventors: Tibor A. Rauch, Oak Park, IL (US); Attila Balog, Szeged (HU); Timea Ocsko, Chicago, IL (US)

(73) Assignee: RUSH UNIVERSITY MEDICAL CENTER, Chicago, IL (US)

( * ) Notice: Subject to any disclaimer, the term of this patent is extended or adjusted under 35 U.S.C. 154(b) by 759 days.

(21) Appl. No.: 16/040,204

(22) Filed: Jul. 19, 2018

(65) Prior Publication Data
US 2019/0022099 A1 Jan. 24, 2019

Related U.S. Application Data

(60) Provisional application No. 62/534,972, filed on Jul. 20, 2017.

(51) Int. Cl.
| | |
|---|---|
| *A61P 37/06* | (2006.01) |
| *A61K 31/52* | (2006.01) |
| *C12N 15/113* | (2010.01) |
| *C12Q 1/6883* | (2018.01) |
| *G01N 33/50* | (2006.01) |

(52) U.S. Cl.
CPC .............. *A61K 31/52* (2013.01); *A61P 37/06* (2018.01); *C12N 15/1137* (2013.01); *C12Q 1/6883* (2013.01); *C12Q 2600/106* (2013.01); *C12Q 2600/156* (2013.01); *C12Q 2600/158* (2013.01); *C12Q 2600/172* (2013.01); *G01N 33/5091* (2013.01); *G01N 2800/50* (2013.01); *G01N 2800/52* (2013.01)

(58) Field of Classification Search
None
See application file for complete search history.

(56) References Cited

U.S. PATENT DOCUMENTS

2009/0264300 A1* 10/2009 Franch .................... C40B 40/08
506/4

OTHER PUBLICATIONS

Leclerc et al. Molecular Biology of Methylenetetrahydrofolate Reductase (MTHFR) and Overview of Mutations/Polymorphisms. 2013. Landis Bioscience. 20 pages. (Year: 2013).*
Takeya et al. Multiple single-polynucleotide polymorphisms in the methylenetetrahydrofolate reductase and its truncated pseudogene of 23 inbred strains of mice. 2003. Biochemical and Biophysical Research Communications. vol. 312, p. 480-486. (Year : 2003).*
Hu et al., PennSeq: accurate isoform-specific gene expression quantification in RNA-Seq by modeling non-uniform read distribution. Nucleic Acids Research (2014), 42(3): 1-9 (Year: 2013).*
Fisher Scientific Basic Principles of RT-qPCR, https://www.thermofisher.com/us/en/home/brands/thermo-scientific/molecular-biology/molecular-biology-learning-center/molecular-biology-resource-library/spotlight-articles/basic-principles-rt-qpcr.html, [retrieved Mar. 28, 2023] (Year: 2023).*
Adams et al., A Beginner's Guide to RT-PCR, qPCR, and RT-qPCR. Biochem (Lond) (2020), 42 (3): 48-53 (Year: 2020).*
Bustin et al., The MIQE Guidelines: Minimum Information for Publication of Quantitative Real-Time PCR Experiments. Clinical Chemistry (2009), 55: 611-622 (Year: 2009).*
MTHFR methylenetetrahydrofolate reductase https://www.ncbi.nlm.nih.gov/gene/4524 [retrieved Nov. 28, 2023] (Year: 2023).*
Meethal, SV et al., "Folate and epigenetic mechanisms in neural tube development and defects", *Childs Nerv Syst*, vol. 29, 2013, pp. 1427-1433.
Kang, SS et al., "Thermolabile Methylenetetrahydrofolate Reductase: an Inherited Risk Factor for Coronary Artery Disease", *Am J Hum Genet*, vol. 48, 1991, pp. 536-545.
Goyette, P. et al., "Human methylenetetrahydrofolate reductase: isolation of cDNA, mapping and mutation identification", *Nat Genet*, vol. 7, 1994, pp. 195-200.
Skibola, CF et al. "Polymorphisms in the methylenetetrahydrofolate reductase gene are associated with susceptibility to acute leukemia in adults", *Proc Natl Acad Sci*, vol. 96, No. 22, 1999, pp. 12810-12815.
Lee, MS et al., "MTHFR polymorphisms, folate intake and carcinogen DNA adducts in the lung", *Int J Cancer*, vol. 131, 2012, pp. 1203-1209.
Ma, J et al., "Methylenetetrahydrofolate Reductase Polymorphism, Dietary Interactions, and Risk of Colorectal Cancer", *Cancer Res*, vol. 57, 1997, pp. 1098-1102.
Shi, H et al., "Study on Environmental Causes and SNPs of MTHFR, MS and CBS Genes Related to Congenital Heart Disease", *PLoS One*, vol. 10, 2015, pp. 1-10.
Toffoli, G et al. "Pharmacogenetic relevance of MTHFR polymorphisms", *Pharmacogenomics*, vol. 9, No. 9,2008, pp. 1195-1206.
Pedroza, LS et al., "Systemic lupus erythematosus: association with KIR and SLC11A1 polymorphisms, ethnic predisposition and influence in clinical manifestations at onset revealed by ancestry genetic markers in an urban Brazilian population", *Lupus*, vol. 20, 2011, pp. 265-273.
Preiss, JC et al., "Use of methotrexate in patients with inflammatory bowel diseases", *Clin Exp Rheumatol*, vol. 28, Suppl. 61, 2010, pp. S151-S155.
Yang, KM et al., "Methylenetetrahydrofolate reductase C677T gene polymorphism and essential hypertension: a meta-analysis of 10,415 subjects", *Biomed Rep*, vol. 2, 2014, pp. 699-708.

(Continued)

*Primary Examiner* — Celine X Qian
*Assistant Examiner* — Catherine Konopka
(74) *Attorney, Agent, or Firm* — Barnes & Thornburg LLP (57) ABSTRACT

The present invention generally relates to methods of determining susceptibility of a subject to developing an inflammatory disorder and to methods of treating the disorder based on the subject's susceptibility. In one embodiment, the method includes determining expression levels of full-length MTHFR encoding mRNA and shortened MTHFR encoding mRNA initiated at intron 3 in a cell from the subject.

8 Claims, 5 Drawing Sheets

Specification includes a Sequence Listing.

(56) References Cited

OTHER PUBLICATIONS

Niu, W et al., "An updated meta-analysis of methylenetetrahydrofolate reductase gene 677C/T polymorphism with diabetic nephropathy and diabetic retinopathy", Diabetes Res Clin Pract, vol. 95, 2012 pp. 110-118.
Parmeggiani, F et al. "Predictive role of C677T MTHFR polymorphism in variable efficacy of photodynamic therapy for neovascular age-related macular degeneration", Pharmacogenomics, vol. 10, No. 1, 2009, pp. 81-95.
Wu, X et al. Folate metabolism gene polymorphisms MTHFR C677T and A1298C and risk for preeclampsia: a meta-analysis, J Assist Reprod Genet, vol. 32, 2015, pp. 797-805.
Yang, Y et al., "Association between MTHFR C677T Polymorphism and Neural Tube Defect Risks: a Comprehensive Evaluation in Three Groups of NTD Patients, Mothers, and Fathers", Birth Defects Res, vol. 103, 2015, pp. 488-500.
Meadows, DN et al., "Increased Resistance to Malaria in Mice with Methylenetetrahydrofolate Reductase (Mthfr) Deficiency Suggests a Mechanism for Selection of the MTHFR 677C>T (c.665C>T) Variant", Hum Mutat, vol. vol. 35, No. 5, 2014, pp. 594-600.
Lea, RA, "The methylenetetrahydrofolate reductase gene variant C677T influences suscelgtibility to migraine with aura", BMC Med, vol. 2, 2004, 8 pgs.
Roffman, J et al., "Effects of the methylenetetrahydrofolate reductase (MTHFR) C677T polymorphism on executive function in schizophrenia", Schizophr Res, vol. 92, 2007, pp. 181-188.
Frosst, P et al., "A candidate genetic risk factor for vascular disease: a common mutation in methylenetetrahydrofolate reductase", Nat Genet, vol. 10, 1995, pp. 111-11.
Maurano, MT et al. "Systematic Localization of Common Disease-Associated Variation in Regulatory DNA", Science, vol. 337, 2012, pp. 1190-1195.
Mercer, TR et al., "DNase Ihypersensitive exons colocalize with promoters and distal regulatory elements", Nat Genet, vol. 45, No. 8, 2013, pp. 852-859.
Stergachis, AB et al. "Exonic Transcription Factor Binding Directs Codon Choice and Affects Protein Evolution", Science, vol. 342, 2013, pp. 1367-1372.
Yadav, VK et al., "Significance of duon mutations in cancer genomes", Sci Rep, vol. 6, 2016, 9 pgs.
Robinson, WH et al., "Biomarkers to guide clinical therapeutics in rheumatology?", Curr Opin Rheumatol, vol. 28, No. 2, 2016, pp. 168-175.
Mohan, C et al., "Biomarkers in rheumatic diseases: how can they facilitate diagnosis and assessment of disease activity?", BMJ, vol. 351, 2015, 13 pgs.
Fransen, J et al., "The Disease Activity Score and the EULAR Pesponse Criteria", Rheum Dis Clin N Am, vol. 35, 2009, pp. 745-757.
Waaler, E, "On the Occurrence of a Factor in Human Serum Activating the Specific Agglutintion of Sheep Blood Corpuscles", originally dated 1940, reprinted in 2007 from APMIS, vol. 115, 422-438.
Schellekens, GA et al., "Citrulline is an essential constituent of antigenic determinants recognized by rheumatoid arthritis-specific autoantibodies", J Clin Invest, vol. 101, No. 1, 1998, pp. 273-281.
Arana, R et a., "Antibodies to native and denatured deoxyribonucleic acid in systemic lupus erythematosus", J Clin Invest, vol. 46, No. 11, 1967, pp. 1867-1882.
Czompoly, T et al., "Anti-topoisomerase I autoantibodies in systemic sclerosis", Autoimmun Rev, vol. 8, 2009, pp. 692-696.
Brouwer, R et al., "Autoantibody profiles in the sera of European patients with myositis", Ann Rheum Dis, vol. 60, 2001, pp. 116-123.
Shiozawa, K et al., "MMP-3 as a predictor for structural remission in RA patients treated with MTX monotherapy", Arthritis Res Ther, vol. 18, 2016, 9 pgs.
Carrier, N et al., "Serum levels of 14-3-3η protein supplement C-reactive protein and rheumatoid arthritis-associated antibodies to predict clinical and radiographic outcomes in a prospective cohort of patients with recent-onset inflammatory polyarthritis", Arthritis Res Ther, vol. 18, 2016, 14 pgs. 16.
Morris, DL et al., "Genome-wide association meta-analysis in Chinese and European individuals identifies ten new loci associated with systemic lupus erythematosus", Nat Genet, vol. 48, No. 8, 2016, pp. 940-946.
Okada, Y et al., "Genetics of rheumatoid arthritis contributes to biology and drug discovery", Nature, vol. 506, 2014, 21 pgs.
Oswald,, M et al., "Modular Analysis of Peripheral Blood Gene Expression in Rheumatoid Arthritis Captures Reproducible Gene Expression Changes in Tumor Necrosis Factor Responders", Arthritis Rheumatol, vol. 67, No. 2, 2015, pp. 344-351.
Gorlick, R et al., "Intrinsic and Acquired Resistance to Methotrexate in Acute Leukemia", N Engl J Med, vol. 335, No. 14, 1996, pp. 1041-1048.
Albrecht, K et al., "Side effects and management of side effects of methotrexate in rheumatoid arthritis", Clin Exp Rheumatol, vol. 28, Suppl 61, 2010, pp. S95-S101.
Romao, VC et al., "Old drugs, old problems: where do we stand in prediction of rheumatoid arthritis responsiveness to methotrexate and other synthetic DMARDs?", BMC Med, vol. 11, 2013, 24 pgs.
Van Ede, AE et al., "The C677T Mutation in the Methylenetetrahydrofolate Reductase Gene: a Genetic Risk Factor for Methotrexate Related Elevation of Liver Enzymes in Rheumatoid Arthritis Patients", Arthritis Rheum, vol. 44, No. 11, 2001, pp. 2525-2530.
Taniguchi, A et al., "Validation of the associations between single nucleotide polymorphisms or haplotypes and responses to disease modifying antirheumatic drugs in patients with rheumatoid arthritis: a proposal for prospective pharmacogenomic study in clinical practice", Pharmacogenet Genomics, vol. 17, No. 6, 2007, pp. 383-390.
Kim, SK et al., "Cost-Effectiveness Analysis of MTHFR Polymorphism Screening by Polymerase Chain Reaction in Korean Patients with Rheumatoid Arthritis Receiving Methotrexate", J Rheumatol, vol. 33, No. 7, 2006, pp. 1266-1274.
Fisher, MC et al., "Metaanalysis of Methylenetetrahydrofolate Reductase (MTHFR) Polymorphisms Affecting Methotrexate Toxicity", J Rheumatol, vol. 36, No. 3, 2009, pp. 539-545.
Owen, SA et al., "MTHFR gene polymorphisms and outcome of methotrexate treatment in patients with rheumatoid arthritis: analysis of key polymorphisms and meta-analysis of C677T and A1298C polymorphisms", Pharmacogenomics J, vol. 13, 2013, pp. 137-147.
Glant, TT et al., "Differentially Expressed Epigenome Modifiers, Including Aurora Kinases A and B, in Immune Cells in Rheumatoid Arthritis in Humans and Mouse Models", Arthritis Rheum, vol. 65, No. 7, 2013, pp. 1725-1735.
Van den, Hoogen F et al., "2013 Classification Criteria for Sytemic Sclerosis: an American College of Rheumatology/European League against Rheumatism collaborative initiative", Arthritis Rheum, vol. 65, No. 11, 2013, pp. 2737-2747.
Hochberg, MC, "Updating the American College of Rheumatology Revised Criteria for the Classification of Systemic Lupus Erythematosus", Arthritis Rheum, vol. 40, No. 9, 1997, pp. 1725.
Campbell, I, "Chi-squared and Fisher-Irwin tests of two-by-two tables with small sample recommendations", Stat Med, vol. 26, 2007, pp. 3661-3675.
Zhou, VW et al., "Charting histone modifications and the functional organization of mammalian genomes", Nat Rev Genet, vol. 12, 2011, pp. 7-18.
Sloan, CA et al., "ENCODE data at the ENCODE portal", Nucleic Acids Res, vol. 44, 2016, pp. D726-D732.
Schaefer, BC, "Revolutions in Rapid Amplification of cDNA Ends: New Strategies for Polymerase Chain Reaction Cloning of Full-Length cDNA Ends", Anal Biochem, vol. 227, 1995, pp. 255-273.
Jencks, DA et al., "Allosteric Inhibition of Methylenetetrahydrofolate Reductase by Adenosylmethionine. Effects of Adenosylmethionine and NADPH on the equilibrium between active and inactive forms of the enzyme and on the kinetics of approach to equilibrium", J Biol Chem, vol. 262, No. 6, 1987, pp. 2485-2493.
Goldberg, T et al., "LocTree2 predicts localization for all domains of life", Bioinformatics, vol. 28, 2012, pp. i458-i465.

(56) References Cited

OTHER PUBLICATIONS

Gaughan, DJ et al., "The human and mouse methylenetetrahydrofolate reductase (MTH FR) genes: genomic organization, mRNA structure and linkage to the CLCN6 gene", *Gene*, vol. 257, 2000, pp. 279-289.

Homberger, A et al, "Genomic structure and transcript variants of the human methylenetetrahydrofolate reductase gene", *Eur J Hum Genet*, vol. 8, 2000, pp. 725-729.

Pickell, L et al., "Targeted insertion of two Mthfr promoters in mice reveals temporal- and tissue-specific regulation", *Mamm Genome*, vol. 22, 2011, pp. 635-647.

Tran, P et al., "Multiple transcription start sites and alternative splicing in the methylenetetrahydrofolate reductase gene result in two enzyme isoforms", *Mamm Genome*, vol. 13, 2002, pp. 483-492.

Salazar, J et al., "Polymorphisms in genes involved in the mechanism of action of methotrexate: are they associated with outcome in rheumatoid arthritis patients?", *Pharmacogenomics*, vol. 15, No. 8, 2014, pp. 1079-1090.

Cookson, W et al., "Mapping complex disease traits with global gene expression", *Nat Rev Genet*, vol. 10, 2009, pp. 184-194.

Weinshilboum, R, "Thiopurine pharmacogenetics: clinical and molecular studies of thiopurine methyltransferase", *Drug Metab Dispos*, vol. 29, No. 4, Part 2, 2001, pp. 601-605.

Wallace, DJ et al., "New insights into mechanisms of therapeutic effects of antimalarial agents in SLE", *Nat Rev Rheumatol*, vol. 8, 2012, pp. 522-533.

Younger, J et al., "The use of low-dose naltrexone (LDN) as a novel anti-inflammatory treatment for chronic pain", *J Clin Rheumatol*, vol. 33, 2014, pp. 451-459.

Maltzman, JS et al., "Azathioprine: old drug, new actions", *J Clin Invest*, vol. 111, 2003, pp. 1122-1124.

Lee, SJ et al., "The role of antimalarial agents in the treatment of SLE and lupus nephritis", *Nat Rev Nephrol*, vol. 7, 2011, pp. 718-729.

Taylor, R. Jr. et al., "Naltrexone extended-release injection: an option for the management of opioid abuse", *Subst Abuse Rehabil*, vol. 2, 2011, pp. 219-226.

Ocsko, T et al., "A Novel MTHFR Isoform-based Biomarker fir RA and SLE", *J Mol Biomark Diagn*, vol. 9, Iss No. 4., 2018, 6 pgs.

\* cited by examiner

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
gccatctgca caaagctaag                    20

```
<210> SEQ ID NO 2
<211> LENGTH: 19
<212> TYPE: DNA
<213> ORGANISM: Artificial Sequence
<220> FEATURE:
<223> OTHER INFORMATION: reverse primer

<400> SEQUENCE: 2
gtagccctgg atgggaaag                                                      19

<210> SEQ ID NO 3
<211> LENGTH: 20
<212> TYPE: DNA
<213> ORGANISM: Artificial Sequence
<220> FEATURE:
<223> OTHER INFORMATION: forward primer

<400> SEQUENCE: 3
ataggtgacc agtgggaaga                                                     20

<210> SEQ ID NO 4
<211> LENGTH: 22
<212> TYPE: DNA
<213> ORGANISM: Artificial Sequence
<220> FEATURE:
<223> OTHER INFORMATION: reverse primer

<400> SEQUENCE: 4
cttcacaaag cggaagaatg tg                                                  22

<210> SEQ ID NO 5
<211> LENGTH: 20
<212> TYPE: DNA
<213> ORGANISM: Artificial Sequence
<220> FEATURE:
<223> OTHER INFORMATION: isoform-specific qRT-PCR forward primer (long)

<400> SEQUENCE: 5
gacatctgtg tggcaggtta                                                     20

<210> SEQ ID NO 6
<211> LENGTH: 20
<212> TYPE: DNA
<213> ORGANISM: Artificial Sequence
<220> FEATURE:
<223> OTHER INFORMATION: isoform-specific qRT-PCR reverse primer (long)

<400> SEQUENCE: 6
gctgcgtgat gatgaaatcg                                                     20

<210> SEQ ID NO 7
<211> LENGTH: 22
<212> TYPE: DNA
<213> ORGANISM: Artificial Sequence
<220> FEATURE:
<223> OTHER INFORMATION: isoform-specific qRT-PCR forward primer (short)

<400> SEQUENCE: 7
gtcatcccta ttggcaggtt ac                                                  22

<210> SEQ ID NO 8
<211> LENGTH: 22
<212> TYPE: DNA
<213> ORGANISM: Artificial Sequence
<220> FEATURE:
<223> OTHER INFORMATION: isoform-specific qRT-PCR reverse primer (short)
```

```
<400> SEQUENCE: 8
cagacacctt ctccttcaag tg                                                    22

<210> SEQ ID NO 9
<211> LENGTH: 25
<212> TYPE: DNA
<213> ORGANISM: Artificial Sequence
<220> FEATURE:
<223> OTHER INFORMATION: forward primer for cloning the alternative
      MTHFR promoter

<400> SEQUENCE: 9
gctagcctga tttgcttggc tgctc                                                 25

<210> SEQ ID NO 10
<211> LENGTH: 25
<212> TYPE: DNA
<213> ORGANISM: Artificial Sequence
<220> FEATURE:
<223> OTHER INFORMATION: reverse primer for cloning the alternative
      MTHFR promoter

<400> SEQUENCE: 10
aagcttgctg gatgggaaag atccc                                                 25
```

METHYLENE-TETRAHYDROFOLATE REDUCTASE ISOFORM-BASED BIOMARKER AND METHOD OF USE THEREOF

RELATED APPLICATIONS

The present patent application claims the benefit of the filing date of U.S. Provisional Patent Application No. 62/534,972, filed Jul. 20, 2017, the contents of which are hereby incorporated by reference.

TECHNICAL FIELD

The present invention generally relates to a method of determining susceptibility of a subject to developing an inflammatory disorder and to methods of treating the disorder based on the subject's susceptibility. The invention also relates to method of determining whether a subject is prone to an adverse drug event when treated with disease modifying anti-rheumatic drug. In one embodiment, the method includes determining expression levels of full-length MTHFR encoding mRNA and shortened MTHFR encoding mRNA initiated at intron 3 in a cell from the subject.

BACKGROUND

Methylene-tetrahydrofolate reductase ("MTHFR") plays a role in the folate cycle by catalyzing the conversion of 5,10-methylenetetrahydrofolate into 5-methyltetrahydrofolate, which can be used in various metabolic events such as DNA and protein biosynthesis and epigenetic modifications [1]. The MTHFR gene gained more interest when high plasma homocysteine levels were found in patients with coronary heart disease [2] and the hyperhomocysteinemia was attributed to altered MTHFR activity caused by SNPs [3]. Since then, the field has rapidly expanded and over 4000 publications have focused on MTHFR polymorphism-related questions. Various diseases including different types of cancer [4-6], cardiovascular diseases [7], rheumatoid arthritis ("RA") [8], systemic lupus srythematosus ("SLE") [9], inflammatory bowel disease [10], hypertension [11], diabetes [12], macular degeneration [13], miscarriages [14], neural tube defects [15], malaria [16], migraine [17] and schizophrenia [18] have been investigated for the MTHFR-related SNP alleles.

These publications were based on the assumption that diminished MTHFR activity results from the C677T polymorphism-associated protein structure change but ignored the fact that reduced activity could only be detected after preincubating MTHFR proteins at non-physiological high temperatures [19]. However, recent genome-wide studies reshaped the understanding of SNPs' role in pathogeneses; it was found that the vast majority of the SNPs are located in non-coding regions, therefore, their disease-promoting effects could be only explained by assuming that gene regulatory elements (i.e., TF binding sites) were affected [20, 21]. In addition, the discovery of duons, TF binding sites in protein-coding regions, has practical implications for the interpretation of genetic variations [22, 23]. Indeed, close to 15% of disease associated SNPs identified by GWASs were located within duons and might be directly involved in pathological mechanisms by compromising both regulatory and/or structural functions of proteins. The C677T polymorphism is within a duon and may significantly affect the expression level of the MTHFR gene in addition to altering the amino acid sequence of MTHFR protein.

Molecular biomarkers are measurable indicators of normal and pathogenic processes and might also have the potential to predict favorable responses to therapy [24]. Rheumatology has traditionally relied on biomarkers and some of them have been incorporated into disease classification criteria [25] including erythrocyte sedimentation rate, C-reactive protein [26], rheumatoid factor [27], anticitrullinated protein antibodies [28], various anti-nuclear antibodies [29], anti-topoisomerase I (Scl-70) antibody [30] and anti-synthetase antibody [31]. Several novel molecular and clinical biomarkers have recently been identified, which can help in differential diagnosis, disease subset definition, or predicting the progression of organ damage [32, 33].

Inflammatory rheumatic diseases are typically complex syndromes, therefore, patients in the same disease category can be genetically heterogeneous [34, 35]. Therapeutic agents are usually effective on specific subsets of patients, which underpins the importance of biomarker-driven personalized therapy over uniformized treatment options. Disease-modifying antirheumatic drug ("DMARD") responsiveness-specific biomarkers have not been identified, and although whole-blood transcriptome analysis revealed promising expression panels for anti-TNF therapy responsiveness, no candidate biomarkers have progressed to becoming clinical diagnostic factors [36]. Accordingly, there is a need for biomarkers that can predict the response to immunosuppressive treatments and to particular therapeutic agents.

Methotrexate (MTX) is a first-line treatment option for newly diagnosed RA patients, which acts by inhibiting the folate cycle [37]. However, approximately 30% of RA patients develop MTX-related adverse drug events (ADEs) [38], provoking discontinuation of MTX therapy [39]. In the context of MTX toxicity, the predictive biomarker potential of C677T polymorphisms has been investigated, but have resulted in contradictory conclusions [40-44].

SUMMARY OF THE PREFERRED EMBODIMENTS

In one aspect, the present invention provides a method for determining susceptibility of a subject to developing an inflammatory disorder. The method includes determining expression levels of full-length MTHFR encoding mRNA and shortened MTHFR encoding mRNA initiated at intron 3 in a cell from the subject. The subject is determined to be at an increased risk of developing the inflammatory disorder if the expression level of the shortened MTHFR encoding mRNA compared to the expression level of full-length MTHFR encoding mRNA is elevated above a threshold value. The inflammatory disorder may be, for example, rheumatoid arthritis or systemic lupus erythematosus.

Another aspect of the invention provides a method for treating an inflammatory disorder in a subject in need of such treatment. One embodiment of the method includes determining expression levels of full-length MTHFR encoding mRNA and shortened MTHFR encoding mRNA initiated at intron 3 in a cell from the subject and administering a therapeutic amount of an anti-inflammatory drug to the subject. The drug is administered if the expression level of the shortened MTHFR encoding mRNA compared to the expression level of full-length MTHFR encoding mRNA is elevated above a threshold value.

Another aspect of the invention provides a method for treating an inflammatory disorder in a subject in need of such treatment, the method including determining expression levels of full-length MTHFR encoding mRNA and shortened MTHFR encoding mRNA initiated at intron 3 in a cell from the subject, and administering a therapeutic amount of an anti-inflammatory drug to the subject. The therapeutic amount of an anti-inflammatory drug is administered if the expression level of the shortened MTHFR encoding mRNA compared to the expression level of full-length MTHFR encoding mRNA is not elevated or is elevated above an intermediate range.

BRIEF DESCRIPTION OF THE DRAWINGS

FIG. 1 shows epigenetic signal profiles along the MTHFR gene in the human K562 cell line. Chromatin immunoprecipitation combined with sequencing (ChIP-seq) data downloaded from the Encyclopedia of DNA Elements (ENCODE) database (40). ChIP-seq was performed using anti-H3K4m3, anti-H3K27ac and anti-Pol 2 antibodies. The numbered black boxes refer to the exons of the MTHFR gene, and the encoded domains of MTHFR protein are depicted above the exons. The left-shadowed box indicates the known MTHFR promoter, and the right-shadowed box depicts the alternative promoter.

FIG. 2A: Schematic diagram of the MTHFR gene. Top: genomic structure of the gene is shown. The numbered black boxes refer to the exons. Below the gene: transcript variants (Trc.v1 and Trc.v2) of MTHFR identified in K562 cells. Open boxes indicate the 5' and 3' untranslated regions. Intronic sequences are shown as thin lines. FIG. 2B: Enlarged view of 3' end of intron 3 and exon 4. Asterisk indicates the location of C677T (rs1801133). FIG. 2C: Detection of MTHFR isoforms by Western blotting. Fractionated K562 cell extracts were probed with C-terminus-specific anti-MTHFR antibody. WCE—whole cell extract, CpF—cytoplasmic fraction, Nucl.E—eluted nuclear fraction [nuclear envelope was preserved during elution], Nucl.L.—nuclear lysates [nuclear envelope was destroyed during elution]. Left hand arrows point to cytoplasm-specific MTHFR isoforms. Right hand arrows indicate nucleus-specific MTHFR isoforms. FIG. 2D: Subcellular localization of MTHFR isoforms. Detection of MTHFR isoforms in K562 cells by confocal microscopy. Top left): DAPI stained nucleus, Top right): MTHFR-specific staining with C terminus-specific anti-MTHFR. Botton left): Cell membrane-specific staining with anti-human CD44 antibody, Bar: 10 μm FIG. 3(A-D). Expression of MTHFR isoforms in human tissue and PBMC samples: Isoform specific PCR Ct values were used to calculate the Li/Si scores. The Li/Si score represents the relative expression difference (fold-difference) between the long MTHFR (Li) and short MTHFR isoform (Si). The expression level of the long isoform is considered 1 in each case. Li/Si scores in FIG. 3A—normal human tissue samples, FIG. 3B—PBSCs of control human subjects, FIG. 3C—PBSCs of RA patients and FIG. 3D—PBSCs of SLE patients. Dotted lines mark the class-defining 0.65 and 2.0 Li/Si scores described in the Results.

DETAILED DESCRIPTION OF THE PREFERRED EMBODIMENTS

Definitions

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

The term "therapeutic effect" as used herein means an effect which induces, ameliorates or otherwise causes an improvement in the pathological symptoms, disease progression or physiological conditions associated with a disorder, for example an inflammatory disorder, of a human or veterinary subject. The term "therapeutically effective amount" as used with respect to a drug means an amount of the drug which imparts a therapeutic effect to the human or veterinary subject.

A MTHFR Isoform-Based Biomarker and Method of Use Thereof

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. In the discussions that follow, a number of potential features or selections of assay methods, methods of analysis, or other aspects, are disclosed. It is to be understood that each such disclosed feature or features can be combined with the generalized features discussed, to form a disclosed embodiment of the present invention.

One aspect of the present invention provides a method for determining the susceptibility of a subject to developing an inflammatory disorder. In certain embodiments, the inflammatory disease is rheumatoid arthritis or systemic lupus erythematosus. The subject may be, for example, a human or veterinary subject.

The applicants have identified a new MTHFR isoform ("shortened MTHFR isoform") that encodes a truncated, catalytically-incompetent protein. The shortened isoform is coded by MTHFR encoding mRNA initiated at intron 3 of the full-length gene. Quantitative monitoring of the catalytically active ("full-length MTHFR isoform") and the catalytically incompetent MTHFR isoforms' expression has revealed that the proportion of the two isoforms may be altered in cells from the subject, such as whole blood or peripheral blood mononuclear cells (PBMCs), in a disease-specific manner in subjects having an inflammatory disease.

In one embodiment, the invention provides a method of determining the susceptibility of a subject to developing an inflammatory disorder based on the relative amounts of the MTHFR encoding mRNA coding the two isoforms. For example, a fold expression difference of the full length and shortened isoforms may be used to determine the susceptibility of the subject. In one embodiment, the method includes determining a gene expression index (Li/Si score) based on expression levels of full-length MTHFR encoding mRNA and shortened MTHFR encoding mRNA initiated at intron 3 in a cell from the subject. In another embodiment, the subject is determined to be at an increased risk of developing the inflammatory disorder if the expression level of the shortened MTHFR encoding mRNA compared to the expression level of full-length MTHFR encoding mRNA is elevated above a threshold value or if this parameter falls within a specified range of elevation.

Another aspect of the present invention provides a method of determining the response of a subjects to a DMARD based the relative amounts of the MTHFR encoding mRNA coding the two isoforms. The method may include determining the Li/Si score based on expression levels of full-length MTHFR encoding mRNA and shortened MTHFR encoding mRNA initiated at intron 3 in a cell from the subject. In one embodiment, the subject is determined to be at an increased risk of developing an adverse to a DMARD if the expression level of the shortened MTHFR encoding mRNA compared to the expression level of full-length MTHFR encoding mRNA is elevated above a threshold value or if this parameter falls within a specified range of elevation.

The fold expression difference (e.g. the Li/Si score) may be calculated from qRT-PCR data, which is found to be characteristic for specific subgroups of patients reflecting disease susceptibility and drug response. Several milliliters of peripheral blood provide sufficient amounts of RNA for conducting isoform-specific qRT-PCR and calculating patient-specific fold expression difference. This parameter is the basis of patient classification and prediction of subjects' drug responsiveness. In one embodiment, the Li/Si score calculation is similar to the fold difference calculation in qRT-PCR experiments. Here, the Li/Si score= $2^{Ct\ of\ long\ MTHFR\ Isoform - Ct\ of\ short\ MTHFR\ Isoform}$, where Ct values correspond to qRT-PCR measured threshold cycles.

In one embodiment, subjects are classified as having normal (Class A), intermediately elevated (Class B) or highly elevated (Class C) scores. For example, Class A subject may have Li/Si scores<6.1, <0.62, <0.63, <0.64, <0.65, <0.66, <6.7, <0.68, or <0.69 Class B subjects may have Li/Si scores above the upper and below the lower limits of Class A and Class C subjects respectively, for example between 0.65-2.0 and Class C subjects may have Li/Si scores>1.8, >1.9, >2.0, >2.1, >2.2, >2.3, >2.4, or >2.5.

In another embodiment, normal, intermediately elevated and highly elevated subject classes are set by determining normal (control) range values for subjects not having an immunological disease (e.g. RA or SLE) and/or not subject to adverse drug event (ADEs) primarily to methotrexate.

Methods of Treating an Inflammatory Disease

Another aspect of the invention provides a method for treating an inflammatory disorder in a subject in need of such treatment. The inflammatory disorder may be, for example, rheumatoid arthritis or systemic lupus erythematosus.

In one embodiment, the method includes determining expression levels of full-length MTHFR encoding mRNA and shortened MTHFR encoding mRNA initiated at intron 3 in a cell from the subject, and administering a therapeutic amount of an anti-inflammatory drug to the subject. The drug is administered if the expression level of the shortened MTHFR encoding mRNA compared to the expression level of full-length MTHFR encoding mRNA is elevated above a threshold value or is determined to be in the intermediately elevated class (Class B), determined as disclosed above.

As disclosed herein, the expression levels may be determined by, for example, determining of expression levels of full-length MTHFR encoding mRNA and shortened MTHFR encoding mRNA initiated at intron 3 in a cell from the subject using isoform-specific qRT-PCR. A fold expression difference (e.g. Li/Si score) may be calculated as disclosed above and the drug administered if the Li/Si score is elevated above a specified range or if the Li/Si score falls within a specified range.

The anti-inflammatory drug may be, for example, methotrexate, azathioprine, chloroquine or naltrexone. The drug may be administered orally, or by a subcutaneous, intra-articular, intradermal, intravenous, intraperitoneal or intramuscular route.

Yet another aspect of the invention provides a method for determining whether a subject is prone to an adverse drug event and for treating the subject based on this determination. In one embodiment, the method includes determining expression levels of full-length MTHFR encoding mRNA and shortened MTHFR encoding mRNA initiated at intron 3 in a cell from the subject as in disclosed above.

Subjects found to have a Class A or Class C values based on this parameter are determined not to be prone of an adverse drug event when treated with a therapeutic amount of an anti-inflammatory drug, such as methotrexate, azathioprine, chloroquine or naltrexone. Subjects found to have a parameter in the Class B range are not treated with such a drug or, alternatively, are treated with an alternative administration scheme that limits the possibility of an adverse drug event. In another embodiment, subjects having Class B values are determined to exhibit methotrexate sensitivity and are treated with another type of DMARD, such as sulfasalazine or leflunomide.

When DMARDs do not provide a satisfactory treatment response, specific biologics, such as anti-TNFα, anti-IL-1β, or IL-6 antagonist, are introduced into the treatment regimen. However, anti-TNF inhibitors are only effective in combination with methotrexate treatment. Accordingly, predicted methotrexate sensitivity also implies which biologics can be employed for effective treatment.

Embodiments of the invention will be further described in the following examples, which do not limit the scope of the invention described in the claims.

EXAMPLES

List of abbreviations: 5'RACE: rapid amplification of 5' cDNA end, ADE: adverse drug event, DMARD: disease-modifying antirheumatic drug, GWAS: genome-wide associated study, NSAID: nonsteroidal anti-inflammatory drug, MTX: Methotrexate, Li/Si score: Expression ratio of Long and Short MTHFR isoforms, PBMC: Peripheral blood mononuclear cells, qRT-PCR: quantitative reverse transcription PCR, RA: rheumatoid arthritis, SNP: single-nucleotide polymorphisms, SLE: systemic lupus erythematosus, TF: transcription factor

Example 1

Cell Culture

The K562 cell line (ATTC CCL-243) was cultured in DMEM medium complemented with 10% fetal bovine serum. The cells cultures were maintained in a humidified incubator at 37° C. with 5% CO2 in air.

Example 2

Rapid Amplification of cDNA Ends (5'RACE)

5'RACE was conducted on 1 µg of total RNA isolated from K562 cells using FirstChoice RLM-RACE kit (Thermo-Fisher Scientific, Waltham, MA). Amplified 5' MTHFR transcript ends were cloned into pDrive vector (Qiagen, Carlsbad, CA) and sequenced. Nucleotide sequence data of the newly identified MTHFR transcript variant was deposited into NCBI GenBank (JQ429447).

Example 3

Total RNA Isolation, cDNA Synthesis and Quantitative Reverse Transcription—Polymerase Chain Reaction (qRT-PCR)

All of these procedures were conducted as previously described [45], but using CFX real-time PCR machine (Bio-Rad, Hercules, CA) for quantitative studies. Normal human tissue RNA samples were purchased as FirstChoice® Human Total RNA Survey Panel (Ambion, Austin, TX). Primers for isoform-specific qRT-PCR were: Long_F: 5'-GACATCTGTGTGGCAGGTTA-3' (SEQ ID NO: 5), Long_R: 5'-GCTGCGTGATGATGAAATCG-3' (SEQ ID NO: 6); Short_F: 5'-GTCATCCCTATTGGCAGGTTAC-3' (SEQ ID NO: 7), Short_R: 5'-CAGACACCTTCTCCTTCAAGTG-3' (SEQ ID NO: 8).

Example 4

Western Blotting

K562 subcellular protein fractions were prepared using Nuclei EZ Prep nuclei isolation kit (Sigma-Aldrich, Saint Louis, MO). Western blotting was performed as described before [45]. C-terminal specific anti-MTHFR antibody (GTX88281, Lot. No. 821604005) was purchased from GeneTex (Irvine, CA).

Example 5

Luciferase Reporter Gene Constructs and Assays

The two different C677T alleles carrying intronic promoters were PCR amplified from genomic DNA. The amplified 489 bps long core promoter regions were cloned into pGL4.19 Luciferase reporter vector (Promega, Madison, WI) and nucleotide sequence of the clones were verified by Sanger sequencing. Primers used for cloning the alternative MTHFR promoter were: 5'-GCTAGCCTGATTTGCTTGGCTGCTC-3' (SEQ ID NO: 9) and 5'-AAGCTTGCTGGATGGGAAAGATCCC-3' (SEQ ID NO: 10). Transient transfection of K562 cells: 5×106 cells in E buffer (2 mM MgCl2, 20 mM Tris-HCl pH 7.43, 50 mM trehalose and 135 mM KCl) were electroporated using Bio-Rad GenePulser II (300V, 950 µF at RT) in the presence of 24 µg of plasmid DNA. Cells were recovered after electroshock treatment in 3 ml of prewarmed medium at room temperature for 20 minutes and cultured further in 6-well plates for 24 hours. Cells were harvested, washed with PBS and lysed in 400 µl of 1× Cell Culture Lysis Reagent (Promega, Medison, WI). Luciferase activity was measured by using 20 µl of lysate and 100 µl of Luciferase Assay Reagent (Promega, Medison, WI) in Single Tube Luminometer (Titertek-Berthold, Pforzheim, Germany).

Example 6

Immunofluorescence Microscopy

K562 cells were fixed and incubated with IM7.8.1-Alexa Fluor 488 conjugated antibody to detect membrane-bound CD44+. After the cells were blocked and stained with C-terminal specific anti-MTHFR antibody (GTX88281, Lot. No. 821604005). Rabbit anti-goat IgG-Texas Red (H+L) (Vector Laboratories, Burlingame, CA) was used as a secondary antibody to detect intracellular MTHFR. Nuclear counterstaining was performed with DAPI. A Zeiss LSM 700 confocal microscope and ZEN 2.3 imaging software were used to detect and analyze subcellular localization of MTHFR isoforms.

Example 7

Human Subjects

All patients and control individuals were recruited under an IRB-approved protocol in Hungary. Signed informed consent was obtained from each subjects.

Controls: Healthy adults aged 19-65 years were recruited from the local community. Exclusion criteria were any chronic conditions including hypertension, allergy, diabetes, obesity and smoking. Control subjects had no infections and did not take NSAID one month before sampling.

Figure 5:
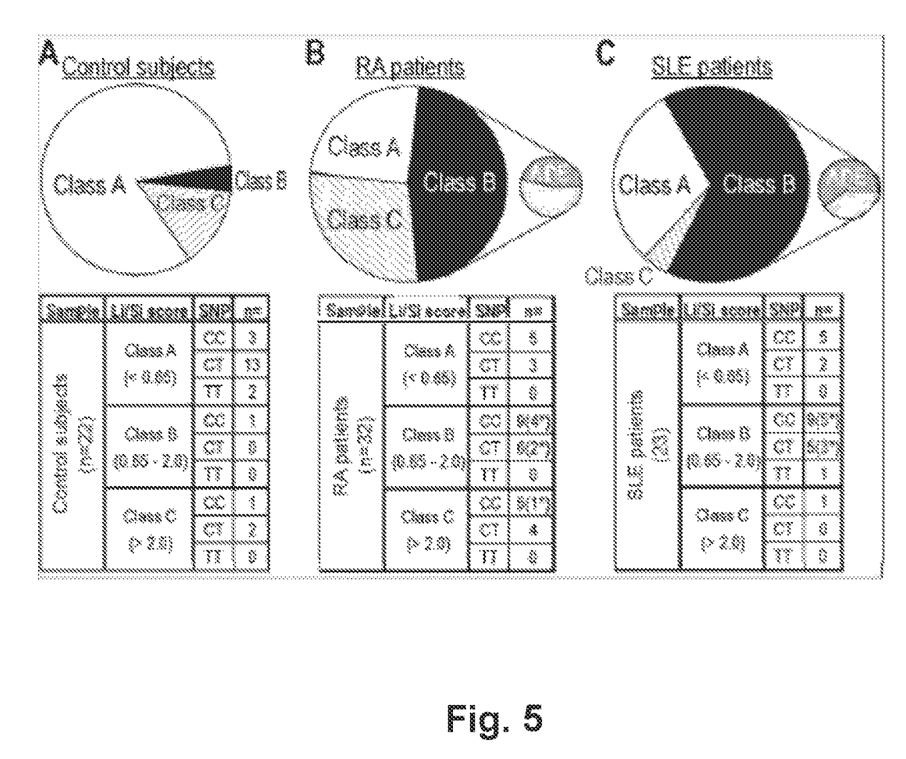
FIG. 5 are Pie charts showing distribution of LI/Si scores for control RA and SLE subjects

Patients: RA patients were diagnosed according to the latest ACR/EULAR classification criteria [46] and MTX therapy and medium dose glucocorticoid therapy was initiated. Twenty three of the 32 RA patients received a variety of DMARDs, containing at least one of the following components: MTX, leflunomide, sulfasalazine or chloroquine. Eleven of the 32 RA patients received biologic therapy including anti-tumor necrosis factor (TNF) or IL6 receptor antagonist. Supplementary Table 1 summarizes the clinical characteristics at the onset of RA diagnosis, history of medication and adverse effects after two years of the diagnosis. SLE patients were diagnosed and classified according to the updated ACR97 criteria [47] at the time of sampling. All SLE patients had a moderate or a severe disease activity. SLEDAI scores were calculated at the time of sampling. Patients were treated with the following medications at onset of the SLE diagnosis and the two years after the diagnosis respectively: methylprednisolone (100%, 78.3%), chloroquine (100%, 78.3%), azathioprine (40.9%, 18.2%), cyclophosphamide (54.5%, 0%), methotrexate (27.3%, 13.7), cyclosporine (4.5%, 4.5%), and mycophenolate mofetil (13.6%, 9.1%), epratuzumab (0%,4.5%), belimumab (0%,4.5%), ustekinumab (0%,4.5%). Supplementary Table 2 summarizes clinical parameters and organ specific involvements of SLE study participants. FIG. 5 shows Pie charts illustrating the distribution of LI/Si scores for control RA and SLE subjects.

Example 8

PBMC Isolation

Peripheral blood mononuclear cells (PBMCs) were separated on a Ficoll gradient within 1 hour after blood samples were obtained from consenting, healthy individuals and from patients naive to treatment with disease-modifying antirheumatic drugs (DMARDs).

Example 9

Determination of Li/Si Score

Li/Si score calculation is similar to the fold difference calculation in qRT-PCR experiments. Accordingly, Li/Si score=$2^{Ct\ of\ long\ MTHFR\ Isoform - Ct\ of\ short\ MTHFR\ Isoform}$, where Ct values correspond to qRT-PCR measured threshold cycles. For example; if a Long MTHFR isoform's Ct value is 27 and a Short MTHFR isoform's Ct value is 29 then Li/Si score is $2^{27-29}$=0.25. This particular Li/Si score implies that the short MTHFR isoform's expression level is ¼ of the long MTHFR isoform.

Example 10

Statistical Analysis

Fisher's exact test was used for calculation of statistical significance of small sample sizes [48].

Example 11

Genotyping of Controls and Patients

Nested PCR was employed to amplify C677T polymorphism carrying regions using the following primer pairs: Outer_F: GCCATCTGCACAAAGCTAAG (SEQ ID NO: 1) & Outer_R: GTAGCCCTGGATGGGAAAG (SEQ ID NO: 2); Inner_F: ATAGGTGACCAGTGGGAAGA (SEQ ID NO: 3) & Inner-R: CTTCACAAAGCGGAAGAATGTG (SEQ ID NO: 4). Purified PCR fragments were directly sequenced and the genotype was determined using FinchTV chromatogram viewer (Geospiza, Inc., Seattle, WA).

Example 12

Results

Figure 1:
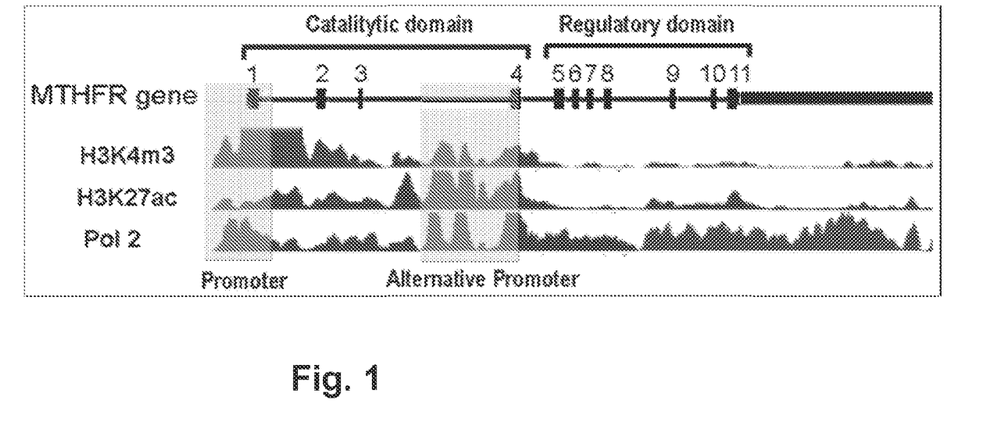

MTHFR could be considered as a gatekeeper enzyme for epigenetic processes [1]; therefore, we investigated how epigenetic signals could affect its expression. Primarily, we focused on histone signals that are known for defining transcriptionally active promoter regions [49]. Several overlapping peaks for histone H3 tri-methylation at lysine 4 (H3K4me3), histone H3 acetylation at lysine 27 (H3K27ac), and RNA polymerase II (Pol 2) were observed in the MTHFR gene in the human K562 cell line [50]. One of the overlapping peaks marked the well-known MTHFR promoter region (FIG. 1, green box) and some additional peaks were observed 6-7 kb downstream from the main promoter (FIG. 1, pink box). These distant peaks located in intron 3 suggested the existence of a supplementary promoter for MTHFR, which had never been investigated. Next, we determined whether the epigenetic signal peak-defined alternative MTHFR promoter region could be transcriptionally active in K562 cells. To this end, transient expression studies were conducted using luciferase reporter gene constructs containing the intronic promoter region. The luciferase activity was 9084±772 fold higher (p>0.01) when the putative MTHFR promoter was fused to the reporter gene and compared to the mock-transfected controls. In addition, we investigated whether a single C to T nucleotide switch that simulates the C667T polymorphism had an effect on luciferase activity. We found that the C-allele construct resulted in 20% (p<0.05) higher luciferase activity than the T-harboring allele, indicating allele-dependent promoter activity.

Figure 2:
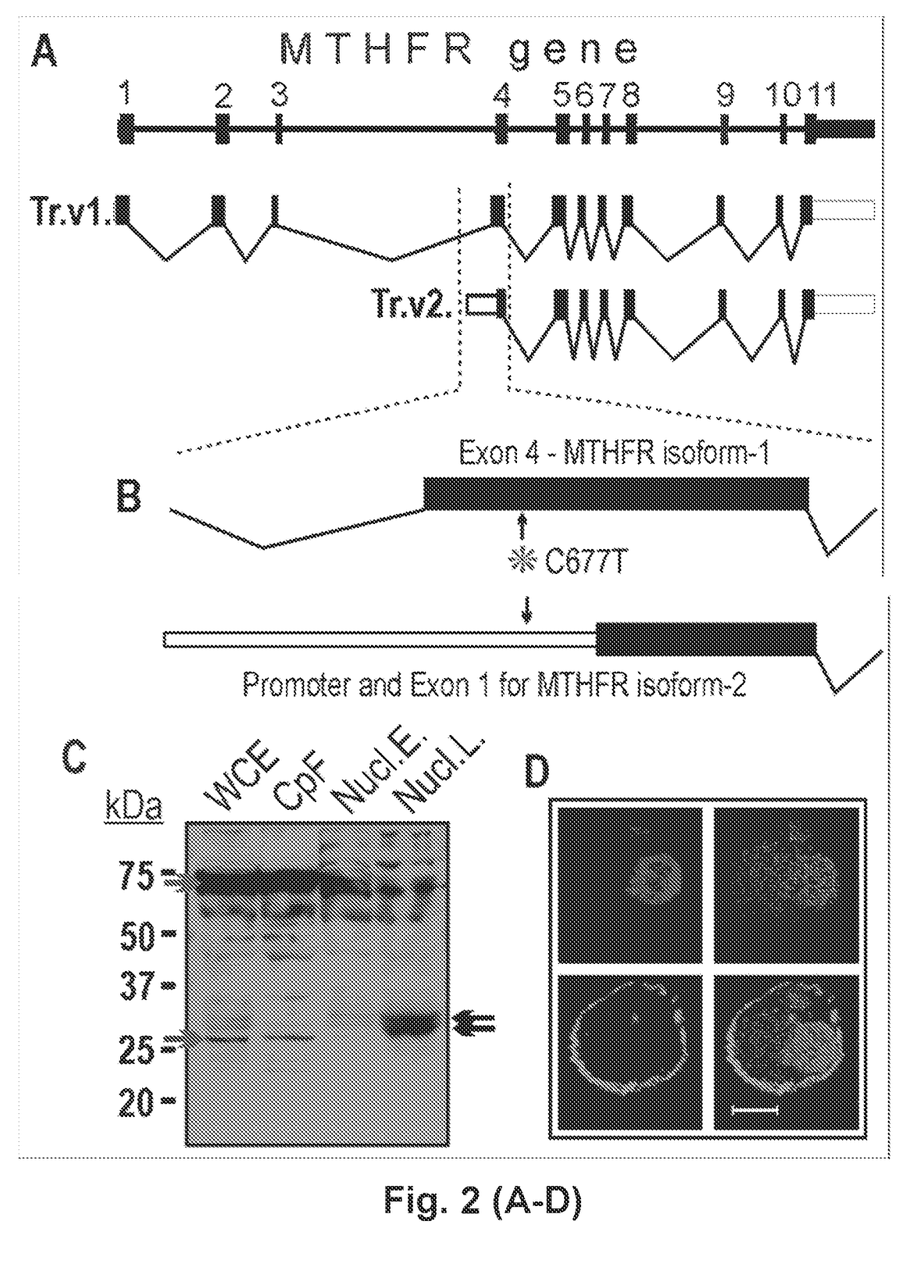
FIG. 2(A-D) shows MTHFR gene transcripts and encoded protein isoforms.

To identify all transcript variants of the MTHFR gene, 5'RACE experiments [51] were carried out (FIG. 2). Two transcript variants were detected, cloned, sequenced and aligned to the human genome (FIGS. 2A and B). One of the transcripts corresponded to the known full-length MTHFR encoding mRNA (Trc.v1), while the other represented a novel mRNA species initiated from intron 3 (Trc.v2). Thus, the first three exons were missing from the Trc.v2 transcript and it could encode only a truncated MTHFR isoform carrying the allosteric regulatory domain of the enzyme [52] (FIGS. 2A and B).

We found that the short MTHFR isoform harbored multiple nuclear localization signals, which suggested that it might have functions in the nuclei [53]. Nuclear localization of the short MTHFR isoform was investigated in subcellular fractions by Western blotting using a C-terminus specific antibody. We found that the full length MTHFR isoform dominated in the cytoplasmic fraction but the short MTHFR isoform could be detected in nuclear lysates (FIG. 2C). The molecular mass of the nuclear MTHFR isoform is smaller (28-30 kDa) than predicted, which can be attributed to a translational mechanism that uses an evolutionarily conserved in-frame start codon located ~650 bp downstream from the 5' end of the Tr.v2 transcript. Nuclear localization of the short MTHFR isoform was confirmed by confocal microscopy (FIG. 2D).

Figure 3:
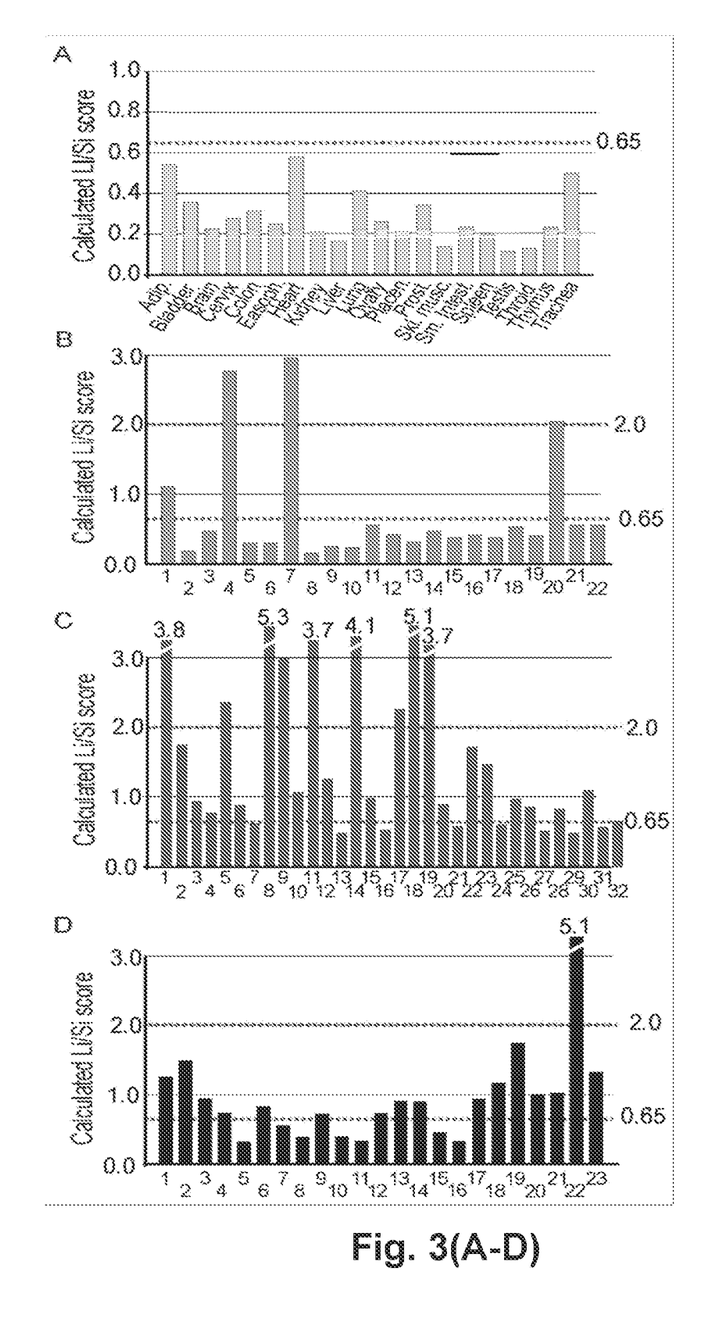

Next, tissue-specificity of the new MTHFR isoform was investigated in 20 normal human tissue samples using isoform-specific qRT-PCR. We did not observe tissue-specific expression of the new MTHFR transcript variant; rather, it was ubiquitously expressed together with the full-length MTHFR coding variant. The expression levels of the two isoforms varied among tissues (FIG. 3A). To compare MTHFR isoform expression between tissues (and later between patients), we introduced the Li/Si score that reflects the fold expression difference between the long (Li) and the short (Si) transcript variants (FIG. 3A). (Li/Si score calculation is detailed in Materials and Methods.) According to these data, the newly described MTHFR isoform is expressed at low levels in all normal tissues together with the full length MTHFR isoform.

A large number of studies investigated the clinical relevance of the MTHFR polymorphisms, but the final conclusions were rather controversial regarding the association with disease susceptibility and drug responsiveness. Since C667T occurs in the newly discovered MTHFR promoter, we compared the transcript variants' (Trc.v1 and Trc.v2) expression in PBMCs isolated from 32 newly diagnosed (treatment naive) patients with active RA, 23 newly diagnosed (treatment naive) patients with active SLE, and 22 healthy age-matched controls (FIG. 3 and Suppl. Patient Table 1 and 2). Li/Si scores were calculated from qRT-PCR values and compared to clinical phenotypes. By using Li/Si scores, control individuals, RA and SLE patients could be divided into 3 classes.

Figure 4:
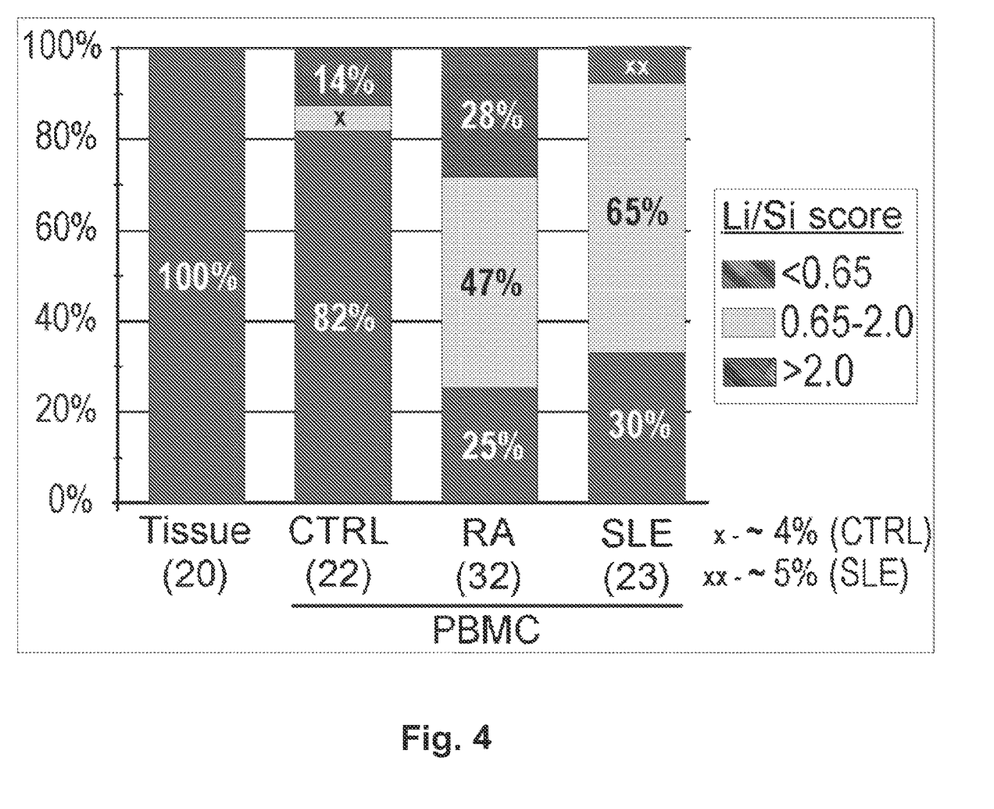
FIG. 4 is a bar chart showing the distribution of Li/Si scores in human samples. Lower region of bar—Li/Si score<0.65. Middle region of bar—Li/Si score 0.65-2.0. Upper region of bar Li/Si score>2.0.

Class-defining threshold values were determined on the basis of the observed Li/Si scores in 20 normal tissue samples (FIG. 3A) and in the PBMC samples of 22 control individuals (FIG. 3B and Table 1). According to these data, Class A individuals had Li/Si scores<0.65, Class B included individuals with Li/Si scores between 0.65-2.0 and Class C individuals had Li/Si scores>2.0. We found that low Li/Si scores (Class A) were characteristic for control individuals (82%, p<0.01), although, similar Li/Si values could also be detected in RA (25%, p<0.01) and SLE (30.4%, p<0.01) patients (FIG. 4 and Tables 2 and 3). The intermediate Li/Si score (Class B) was exclusively characteristic of RA (46.8%, p<0.01) and SLE (65.2%, p<0.01) patients (FIG. 4 and Table 2 & 3). Interestingly, the subjects with high Li/Si values (Class C) were relatively frequent among controls (13.6%, p<0.01) and RA patients (28.1%, p<0.01) but scarce among SLE patients (4.3%, p=0.01) (FIG. 4 and Table 3). In addition, we found that RA and SLE patients with intermediate Li/Si scores (Class B) were prone to ADEs, including hepatotoxicity and gastrointestinal complaints for RA, and gastrointestinal complaints, fever, and hepatitis for SLE patients. RA patients with intermediate Li/Si scores had a 19% chance (p=0.03) of developing ADE, while SLE patients had 39% chance (p<0.01) (Tables 1-3).

Next, we genotyped all subjects by sequencing the C677T polymorphism-carrying region and investigated how allele frequencies and Li/Si scores correlated with diseases. We found that T allele carrying individuals were over-represented among control subjects (77.27%) compared to RA (40%, p<0.05) or SLE (34.7%, p<0.01) patients, but further correlation could not be found between C667T alleles and diseases. In contrast, intermediate Li/Si score defined a unique group of patients with a high probability for susceptibility to both of the autoimmune diseases (RA—46.8%, p<0.01 and SLE—65.2%, p<0.01) (Tables 1-3) and the same class B patients were also prone to ADE. These findings indicated that the C677T polymorphism itself has a limited potential as a biomarker, but the Li/Si scores could indicate susceptibility to diseases (i.e., RA and SLE) and ADE.

Example 13

Conclusions

Epigenetic signal profiles downloaded from the ENCODE database [50] predicted the existence of an intragenic MTHFR promoter, which proved to be active in subsequent gene expression studies (FIGS. 1 and 2). In fact, a few studies reported alternative promoters for the MTHFR gene, but those were mapped upstream from the well-known MTHFR transcription initiation site [54-57]. The MTHFR promoter that we identified was located in intron 3, and the corresponding transcript encoded a truncated MTHFR isoform with unknown function in the nucleus.

What makes the intronic MTHFR promoter even more interesting is that the C677T SNP resides in exon 4 and partially overlaps with the novel promoter (FIG. 2B). Accordingly, this intragenic region is a bona fide duon: (i) it encodes certain part of the full-length MTHFR, and (ii) as part of the intronic promoter, it governs the expression of the truncated MTHFR isoform. Transient expression studies revealed that MTHFR promoter activity could be allele-dependent; the T allele-carrying promoter resulted in 20% lower Luciferase activity than the C allele-harboring promoter. We found that the T allele was more frequently identified in healthy controls than in RA or SLE patients (Tables 1-3). However, the linkage between the T allele and low Li/Si score was not exclusive for healthy individuals since the T allele could also be found in RA and SLE patients with elevated Li/Si scores. Altogether, these findings indicate that the C677T alleles are not the only factors that can define the intronic MTHFR promoter activity. Indeed, a recent study reported a new disease-associated SNP [58] in close proximity to C677T that may also alter the intronic MTHFR promoter activity. It is also reasonable to assume that combinations of genetic variants, rather than a single SNP, determine the promoter activity. By exploring Li/Si scores in 22 control individuals and 55 patients (32 RA and 23 SLE) we took the first steps toward evaluating Li/Si score as a potential biomarker. On the basis of the observed Li/Si scores in control samples, we defined 3 levels (low, intermediate and high Li/Si score classes). Notably, the current threshold values could be further specified by obtaining Li/Si scores from extended patient populations. Although healthy individuals dominantly possess low Li/Si scores, similar values can also be observed in RA and SLE patients (FIG. 4). This observation can be attributed to the polygenic nature of RA and SLE [34, 35], indicating that a number of disease risk loci might be more dominant than the altered MTHFR isoform ratio. To explore the mechanism of pathogenesis behind the MTHFR-related clinical phenotypes, a more complex approach should be employed, including genome-wide SNP and expression analyses (i.e., eQTL analyses) [59]. Intermediate Li/Si scores (Class B) were found to be exclusive for RA and SLE patients, and a subpopulation of these subjects were also prone to ADEs.

Specifically, patients with intermediate Li/Si scores tend to develop hypersensitivity to DMARDs, including MTX [38], azathioprine [60], chloroquine [61] and naltrexone [62]. The link between Li/Si score and MTX toxicity can be explained by the fact that this drug inhibits the folate cycle in which MTHFR plays a role, and the disease-associated imbalance of MTHFR isoform expression might also trigger ADEs. However, the other DMARDs, including azathioprine, chloroquine and naltrexone, are involved in different pathways, and it is unclear how Li/Si scores relate to the adverse reactions to these drugs [63-65]. Nevertheless, regarding the biomarker potential of Li/Si score, it depends on which molecular mechanisms/pathways underlie the investigated rheumatic diseases. High and low Li/Si scores can be observed in both healthy individuals and patients with RA or SLE, which might indicate the significance of other disease risk regions involved in RA and SLE pathogeneses.

Usually, treatments employ dynamic strategies to induce and maintain the lowest possible disease activity and to prevent irreversible joint damage and organ failure in RA and SLE. However, approximately 40% of patients fail to achieve or maintain a response to the low-cost, first-line DMARDs such as MTX. This results in (i) a waste of time by waiting for clinical responses, which can lead to continued joint damage, (ii) unnecessary exposure to potentially toxic drugs, and (iii) a waste of resources. Application of the Li/Si score might help guide clinical decisions regarding therapeutic intervention in several ways by identifying patients with a high tolerance toward DMARDs (Class A and C) who might benefit from an increased dose. On the other hand, individuals with potential ADEs (Class B) could be treated more carefully to minimize DMARD induced toxicity. Since ADE prone individuals constitute a subpopulation among patients with intermediate Li/Si scores (Class B), it will be essential to identify additional factors that could be used to discriminate between the DMARD sensitive and insensitive subjects. The Li/Si score has been investigated here in the context of RA and SLE, but the usefulness of the Li/Si score-based classification in other diseases should be addressed in future studies.

TABLE 1

Li/Si scores in healthy control individuals. Li/Si scores were calculated from qRT-PCR Ct values measured in PBMC samples. Control individuals are sorted by Li/Si scores in ascending order. P-ID refers to subject identification number, SNP: actual genotype of C677T polymorphism.

| Class | P-ID | Gender | SNP | Li/Si |
|---|---|---|---|---|
| A | CTRL-08 | F | CT | 0.16 |
|   | CTRL-02 | M | CT | 0.19 |
|   | CTRL-10 | F | CT | 0.24 |
|   | CTRL-09 | F | CT | 0.26 |
|   | CTRL-06 | F | CC | 0.30 |
|   | CTRL-05 | F | CT | 0.31 |
|   | CTRL-13 | M | TT | 0.32 |
|   | CTRL-15 | M | CC | 0.38 |
|   | CTRL-17 | F | CT | 0.38 |
|   | CTRL-19 | M | CT | 0.41 |
|   | CTRL-16 | F | TT | 0.42 |
|   | CTRL-12 | M | CC | 0.43 |
|   | CTRL-03 | M | CT | 0.48 |
|   | CTRL-14 | F | CT | 0.48 |
|   | CTRL-18 | F | CT | 0.54 |
|   | CTRL-11 | M | CT | 0.56 |
|   | CTRL-22 | M | CT | 0.56 |
|   | CTRL-21 | F | CT | 0.56 |
| B | CTRL-01 | M | CC | 1.12 |
| C | CTRL-20 | F | CC | 2.05 |
|   | CTRL-04 | F | CT | 3.77 |
|   | CTRL-07 | F | CT | 4.96 |

TABLE 2

Li/Si Scores of RA Patients. Li/Si scores were calculated from qRT-PCR Ct values measured in PBMC samples. RA patients are sorted by Li/Si scores in ascending order. P-ID refers to patient identification number, SNP: actual genotype of C677T polymorphism. ADE (adverse drug event): presence (+) or absence (−) of ADE.

| Class | P-ID | Gender | SNP | Li/Si | ADE |
|---|---|---|---|---|---|
| A | RA-13 | F | CT | 0.48 | − |
|   | RA-29 | M | CC | 0.49 | − |
|   | RA-27 | F | CT | 0.51 | − |
|   | RA-16 | F | CC | 0.53 | − |
|   | RA-31 | F | CC | 0.57 | − |
|   | RA-21 | M | CC | 0.58 | − |
|   | RA-24 | F | CT | 0.61 | − |
|   | RA-07 | F | CC | 0.62 | − |
| B | RA-32 | F | CC | 0.65 | + |
|   | RA-04 | M | CC | 0.76 | − |
|   | RA-28 | F | CC | 0.83 | − |
|   | RA-26 | F | CC | 0.86 | + |
|   | RA-06 | F | CT | 0.88 | + |
|   | RA-20 | F | CC | 0.90 | − |
|   | RA-03 | F | CC | 0.94 | − |
|   | RA-25 | F | CT | 0.98 | − |
|   | RA-15 | F | CT | 0.99 | − |
|   | RA-10 | M | CT | 1.07 | − |
|   | RA-30 | F | CC | 1.10 | + |
|   | RA-12 | F | CC | 1.26 | − |
|   | RA-23 | F | CT | 1.47 | − |
|   | RA-22 | M | CT | 1.72 | + |
|   | RA-02 | F | CC | 1.75 | + |
| C | RA-17 | M | CT | 2.26 | − |
|   | RA-05 | F | CT | 2.36 | − |
|   | RA-09 | F | CT | 3.04 | − |
|   | RA-19 | F | CT | 3.70 | − |
|   | RA-11 | M | CC | 3.71 | − |
|   | RA-01 | F | CC | 3.87 | + |
|   | RA-14 | F | CC | 4.10 | − |
|   | RA-18 | M | CC | 8.10 | − |
|   | RA-08 | F | CC | 19.37 | − |

TABLE 3

Li/Si scores in SLE patients. Li/Si scores were calculated from qRT-PCR Ct values measured in PBMC samples. SLE patients are sorted by Li/Si scores in ascending order. P-ID reefers to patient identification number, SNP: actual genotype of C677T polymorphism. ADE (adverse drug event): presence (+) or absence (−) of ADE.

| Class | P-ID | Gender | SNP | Li/Si | ADE |
|---|---|---|---|---|---|
| A | SLE-05 | F | CC | 0.32 | − |
|   | SLE-16 | F | CC | 0.33 | − |
|   | SLE-11 | F | CT | 0.34 | − |
|   | SLE-08 | F | CT | 0.39 | − |
|   | SLE-10 | F | CC | 0.40 | − |
|   | SLE-15 | F | CC | 0.46 | − |
|   | SLE-07 | F | CC | 0.56 | − |
| B | SLE-09 | F | TT | 0.73 | + |
|   | SLE-12 | F | CC | 0.73 | − |
|   | SLE-04 | F | CT | 0.74 | + |
|   | SLE-06 | F | CC | 0.83 | − |
|   | SLE-14 | F | CC | 0.90 | + |
|   | SLE-13 | F | CC | 0.90 | + |
|   | SLE-17 | F | CT | 0.93 | − |
|   | SLE-03 | F | CT | 0.94 | + |
|   | SLE-20 | F | CT | 1.01 | − |
|   | SLE-21 | F | CC | 1.02 | + |
|   | SLE-18 | F | CC | 1.17 | + |
|   | SLE-01 | F | CC | 1.25 | + |
|   | SLE-23 | F | CC | 1.32 | − |
|   | SLE-02 | F | CC | 1.48 | − |
|   | SLE-19 | F | CT | 1.73 | + |
| C | SLE-22 | F | CC | 6.15 | − |

REFERENCES

[1] Meethal S V, Hogan K J, Mayanil C S, Iskandar B J. Folate and epigenetic mechanisms in neural tube development and defects. Childs Nerv Syst 2013; 29:1427-33.

[2] Kang S S, Wong P W, Susmano A, Sora J, Norusis M, Ruggie N. Thermolabile methylenetetrahydrofolate reductase: an inherited risk factor for coronary artery disease. Am J Hum Genet 1991; 48:536-45.

[3] Goyette P, Sumner J S, Milos R, Duncan A M, Rosenblatt D S, Matthews R G et al. Human methylenetetrahydrofolate reductase: isolation of cDNA, mapping and mutation identification. Nat Genet 1994; 7:195-200.

[4] Skibola C F, Smith M T, Kane E, Roman E, Rollinson S, Cartwright R A et al. Polymorphisms in the methylenetetrahydrofolate reductase gene are associated with susceptibility to acute leukemia in adults. Proc Natl Acad Sci USA 1999; 96:12810-5.

[5] Lee M S, Asomaning K, Su L, Wain J C, Mark E J, Christiani D C. MTHFR polymorphisms, folate intake and carcinogen DNA adducts in the lung. Int J Cancer 2011.

[6] Ma J, Stampfer M J, Giovannucci E, Artigas C, Hunter D J, Fuchs C et al. Methylenetetrahydrofolate reductase polymorphism, dietary interactions, and risk of colorectal cancer. Cancer Res 1997; 57:1098-102.

[7] Shi H, Yang S, Liu Y, Huang P, Lin N, Sun X et al. Study on Environmental Causes and SNPs of MTHFR, MS and CBS Genes Related to Congenital Heart Disease. PLoS One 2015; 10:e0128646.

[8] Toffoli G, De M E. Pharmacogenetic relevance of MTHFR polymorphisms. Pharmacogenomics 2008; 9:1195-206.

[9] Pedroza L S, Sauma M F, Vasconcelos J M, Takeshita L Y, Ribeiro-Rodrigues E M, Sastre D et al. Systemic lupus erythematosus: association with KIR and SLC11A1 polymorphisms, ethnic predisposition and influence in clinical manifestations at onset revealed by ancestry genetic markers in an urban Brazilian population. Lupus 2011; 20:265-73.

[10] Preiss J C, Zeitz M. Use of methotrexate in patients with inflammatory bowel diseases. Clin Exp Rheumatol 2010; 28:S151-S155.

[11] Yang K M, Jia J, Mao L N, Men C, Tang K T, Li Y Y et al. Methylenetetrahydrofolate reductase C677T gene polymorphism and essential hypertension: A meta-analysis of 10,415 subjects. Biomed Rep 2014; 2:699-708.

[12] Niu W, Qi Y. An updated meta-analysis of methylenetetrahydrofolate reductase gene 677C/T polymorphism with diabetic nephropathy and diabetic retinopathy. Diabetes Res Clin Pract 2012; 95:110-8.

[13] Parmeggiani F, Gemmati D, Costagliola C, Sebastiani A, Incorvaia C. Predictive role of C677T MTHFR polymorphism in variable efficacy of photodynamic therapy for neovascular age-related macular degeneration. Pharmacogenomics 2009; 10:81-95.

[14] Wu X, Yang K, Tang X, Sa Y, Zhou R, Liu J et al. Folate metabolism gene polymorphisms MTHFR C677T and A1298C and risk for preeclampsia: a meta-analysis. J Assist Reprod Genet 2015; 32:797-805.

[15] Yang Y, Chen J, Wang B, Ding C, Liu H. Association between MTHFR C677T polymorphism and neural tube defect risks: A comprehensive evaluation in three groups of NTD patients, mothers, and fathers. Birth Defects Res A Clin Mol Teratol 2015; 103:488-500.

[16] Meadows D N, Pyzik M, Wu Q, Torre S, Gros P, Vidal S M et al. Increased resistance to malaria in mice with methylenetetrahydrofolate reductase (Mthfr) deficiency suggests a mechanism for selection of the MTHFR 677C>T (c.665C>T) variant. Hum Mutat 2014; 35:594-600.

[17] Lea R A, Ovcaric M, Sundholm J, MacMillan J, Griffiths L R. The methylenetetrahydrofolate reductase gene variant C677T influences susceptibility to migraine with aura. BMC Med 2004; 2:3.

[18] Roffman J L, Weiss A P, Deckersbach T, Freudenreich O, Henderson D C, Purcell S et al. Effects of the methylenetetrahydrofolate reductase (MTHFR) C677T polymorphism on executive function in schizophrenia. Schizophr Res 2007; 92:181-8.

[19] Frosst P, Blom H J, Milos R, Goyette P, Sheppard C A, Matthews R G et al. A candidate genetic risk factor for vascular disease: a common mutation in methylenetetrahydrofolate reductase. Nat Genet 1995; 10:111-3.

[20] Maurano M T, Humbert R, Rynes E, Thurman R E, Haugen E, Wang H et al. Systematic localization of common disease-associated variation in regulatory DNA. Science 2012; 337:1190-5.

[21] Mercer T R, Edwards S L, Clark M B, Neph S J, Wang H, Stergachis A B et al. DNase I hypersensitive exons colocalize with promoters and distal regulatory elements. Nat Genet 2013; 45:852-9.

[22] Stergachis A B, Haugen E, Shafer A, Fu W, Vernot B, Reynolds A et al. Exonic transcription factor binding directs codon choice and affects protein evolution. Science 2013; 342:1367-72.

[23] Yadav V K, Smith K S, Flinders C, Mumenthaler S M, De S. Significance of duon mutations in cancer genomes. Sci Rep 2016; 6:27437.

[24] Robinson W H, Mao R. Biomarkers to guide clinical therapeutics in rheumatology? Curr Opin Rheumatol 2016; 28:168-75.

[25] Mohan C, Assassi S. Biomarkers in rheumatic diseases: how can they facilitate diagnosis and assessment of disease activity? BMJ 2015; 351:h5079.

[26] Fransen J, van Riel P L. The Disease Activity Score and the EULAR response criteria. Rheum Dis Clin North Am 2009; 35:745-viii.

[27] Waaler E. On the occurrence of a factor in human serum activating the specific agglutintion of sheep blood corpuscles. 1939. APMIS 2007; 115:422-38.

[28] Schellekens G A, de Jong B A, van den Hoogen F H, van de Putte L B, van Venrooij W J. Citrulline is an essential constituent of antigenic determinants recognized by rheumatoid arthritis-specific autoantibodies. J Clin Invest 1998; 101:273-81.

[29] Arana R, Seligmann M. Antibodies to native and denatured deoxyribonucleic acid in systemic lupus erythematosus. J Clin Invest 1967; 46:1867-82.

[30] Czompoly T, Simon D, Czirjak L, Nemeth P. Anti-topoisomerase I autoantibodies in systemic sclerosis. Autoimmun Rev 2009; 8:692-6.

[31] Brouwer R, Hengstman G J, Vree E W, Ehrfeld H, Bozic B, Ghirardello A et al. Autoantibody profiles in the sera of European patients with myositis. Ann Rheum Dis 2001; 60:116-23.

[32] Shiozawa K, Yamane T, Murata M, Yoshihara R, Tsumiyama K, Imura S et al. MMP-3 as a predictor for structural remission in RA patients treated with MTX monotherapy. Arthritis Res Ther 2016; 18:55.

[33] Carrier N, Marotta A, de Brum-Fernandes A J, Liang P, Masetto A, Menard H A et al. Serum levels of 14-3-3eta protein supplement C-reactive protein and rheumatoid arthritis-associated antibodies to predict clinical and radiographic outcomes in a prospective cohort of patients with recent-onset inflammatory polyarthritis. Arthritis Res Ther 2016; 18:37.

[34] Morris D L, Sheng Y, Zhang Y, Wang Y F, Zhu Z, Tombleson P et al. Genome-wide association meta-analysis in Chinese and European individuals identifies ten new loci associated with systemic lupus erythematosus. Nat Genet 2016; 48:940-6.

[35] Okada Y, Wu D, Trynka G, Raj T, Terao C, Ikari K et al. Genetics of rheumatoid arthritis contributes to biology and drug discovery. Nature 2014; 506:376-81.

[36] Oswald M, Curran M E, Lamberth S L, Townsend R M, Hamilton J D, Chernoff D N et al. Modular analysis of peripheral blood gene expression in rheumatoid arthritis captures reproducible gene expression changes in tumor necrosis factor responders. Arthritis Rheumatol 2015; 67:344-51.

[37] Gorlick R, Goker E, Trippett T, Waltham M, Banerjee D, Bertino J R. Intrinsic and acquired resistance to methotrexate in acute leukemia. N Engl J Med 1996; 335:1041-8.

[38] Albrecht K, Muller-Ladner U. Side effects and management of side effects of methotrexate in rheumatoid arthritis. Clin Exp Rheumatol 2010; 28:S95-101.

[39] Romao V C, Canhao H, Fonseca J E. Old drugs, old problems: where do we stand in prediction of rheumatoid arthritis responsiveness to methotrexate and other synthetic DMARDs? BMC Med 2013; 11:17.

[40] van Ede A E, Laan R F, Blom H J, Huizinga T W, Haagsma C J, Giesendorf B A et al. The C677T mutation in the methylenetetrahydrofolate reductase gene: a genetic risk factor for methotrexate related elevation of liver enzymes in rheumatoid arthritis patients. Arthritis Rheum 2001; 44:2525-30.

[41] Taniguchi A, Urano W, Tanaka E, Furihata S, Kamitsuji S, Inoue E et al. Validation of the associations between single nucleotide polymorphisms or haplotypes and responses to disease modifying antirheumatic drugs in patients with rheumatoid arthritis: a proposal for prospective pharmacogenomic study in clinical practice. Pharmacogenet Genomics 2007; 17:383-90.

[42] Kim S K, Jun J B, El-Sohemy A, Bae S C. Cost-effectiveness analysis of MTHFR polymorphism screening by polymerase chain reaction in Korean patients with rheumatoid arthritis receiving methotrexate. J Rheumatol 2006; 33:1266-74.

[43] Fisher M C, Cronstein B N. Metaanalysis of methylenetetra hydrofolate reductase (MTHFR) polymorphisms affecting methotrexate toxicity. J Rheumatol 2009; 36:539-45.

[44] Owen S A, Lunt M, Bowes J, Hider S L, Bruce I N, Thomson W et al. MTHFR gene polymorphisms and outcome of methotrexate treatment in patients with rheumatoid arthritis: analysis of key polymorphisms and meta-analysis of C677T and A1298C polymorphisms. Pharmacogenomics J 2013; 13:137-47.

[45] Giant T T, Besenyei T, Kadar A, Kurko J, Tryniszewska B, Gal J et al. Differentially expressed epigenome modifiers, including aurora kinases A and B, in immune cells in rheumatoid arthritis in humans and mouse models. Arthritis Rheum 2013; 65:1725-35.

[46] van den Hoogen F, Khanna D, Fransen J, Johnson S R, Baron M, Tyndall A et al. 2013 classification criteria for systemic sclerosis: an American College of Rheumatology/European League against Rheumatism collaborative initiative. Arthritis Rheum 2013; 65:2737-47.

[47] Hochberg M C. Updating the American College of Rheumatology revised criteria for the classification of systemic lupus erythematosus. Arthritis Rheum 1997; 40:1725.

[48] Campbell I. Chi-squared and Fisher-Irwin tests of two-by-two tables with small sample recommendations. Stat Med 2007; 26:3661-75.

[49] Zhou V W, Goren A, Bernstein B E. Charting histone modifications and the functional organization of mammalian genomes. Nat Rev Genet 2011; 12:7-18.

[50] Sloan C A, Chan E T, Davidson J M, Malladi V S, Strattan J S, Hitz B C et al. ENCODE data at the ENCODE portal. Nucleic Acids Res 2016; 44:D726-D732.

[51] Schaefer B C. Revolutions in rapid amplification of cDNA ends: new strategies for polymerase chain reaction cloning of full-length cDNA ends. Anal Biochem 1995; 227:255-73.

[52] Jencks D A, Mathews R G. Allosteric inhibition of methylenetetrahydrofolate reductase by adenosylmethionine. Effects of adenosylmethionine and NADPH on the equilibrium between active and inactive forms of the enzyme and on the kinetics of approach to equilibrium. J Biol Chem 1987; 262:2485-93.

[53] Goldberg T, Hamp T, Rost B. LocTree2 predicts localization for all domains of life. Bioinformatics 2012; 28:i458-i465.

[54] Gaughan D J, Barbaux S, Kluijtmans L A, Whitehead A S. The human and mouse methylenetetrahydrofolate reductase (MTHFR) genes: genomic organization, mRNA structure and linkage to the CLCN6 gene. Gene 2000; 257:279-89.

[55] Homberger A, Linnebank M, Winter C, Willenbring H, Marquardt T, Harms E et al. Genomic structure and transcript variants of the human methylenetetrahydrofolate reductase gene. Eur J Hum Genet 2000; 8:725-9.

[56] Pickell L, Wu Q, Wang X L, Leclerc D, Friedman H, Peterson A C et al. Targeted insertion of two Mthfr promoters in mice reveals temporal- and tissue-specific regulation. Mamm Genome 2011; 22:635-47.

[57] Tran P, Leclerc D, Chan M, Pai A, Hiou-Tim F, Wu Q et al. Multiple transcription start sites and alternative splicing in the methylenetetrahydrofolate reductase gene result in two enzyme isoforms. Mamm Genome 2002; 13:483-92.

[58] Salazar J, Moya P, Altes A, Diaz-Torne C, Casademont J, Cerda-Gabaroi D et al. Polymorphisms in genes involved in the mechanism of action of methotrexate: are they associated with outcome in rheumatoid arthritis patients? Pharmacogenomics 2014; 15:1079-90.

[59] Cookson W, Liang L, Abecasis G, Moffatt M, Lathrop M. Mapping complex disease traits with global gene expression. Nat Rev Genet 2009; 10:184-94.

[60] Weinshilboum R. Thiopurine pharmacogenetics: clinical and molecular studies of thiopurine methyltransferase. Drug Metab Dispos 2001; 29:601-5.

[61] Wallace D J, Gudsoorkar V S, Weisman M H, Venuturupalli S R. New insights into mechanisms of therapeutic effects of antimalarial agents in SLE. Nat Rev Rheumatol 2012; 8:522-33.

[62] Younger J, Parkitny L, McLain D. The use of low-dose naltrexone (LDN) as a novel anti-inflammatory treatment for chronic pain. Clin Rheumatol 2014; 33:451-9.

[63] Maltzman J S, Koretzky G A. Azathioprine: old drug, new actions. J Clin Invest 2003; 111:1122-4.

[64] Lee S J, Silverman E, Bargman J M. The role of antimalarial agents in the treatment of SLE and lupus nephritis. Nat Rev Nephrol 2011; 7:718-29.

[65] Taylor R, Jr., Raffa R B, Pergolizzi J V, Jr. Naltrexone extended-release injection: an option for the management of opioid abuse. Subst Abuse Rehabil 2011; 2:219-26.

We claim:

1. A method for determining sensitivity in a subject to a treatment, the method comprising:
   determining expression levels of a full-length MTHFR encoding mRNA and a truncated MTHFR encoding mRNA in a cell from the subject comprising:
   (a) performing isoform-specific qRT-PCR of the full-length MTHFR encoding mRNA using a first primer consisting of SEQ ID NO 5 and a second primer consisting of SEQ ID NO 6,
   (b) performing isoform-specific qRT-PCR of the truncated MTHFR encoding mRNA using a third primer consisting of SEQ ID NO 7 and a fourth primer consisting of SEQ ID NO 8,
   c) calculating a Li/Si score using the Ct values generated in steps (a) and (b); and
   determining the patient is not a candidate for treatment with one or more of methotrexate, azathioprine, chloroquine, or naltrexone;
   administering a treatment comprising one or more anti-inflammatory drugs excluding methotrexate, azathioprine, chloroquine, or naltrexone;
   wherein the Li/Si score is between a threshold value of 0.65 and 2.0.

2. A method for treating an inflammatory disorder in a subject in need of such treatment and at risk for an adverse event, the method comprising:
   determining expression levels of a full-length MTHFR encoding mRNA and a truncated MTHFR encoding mRNA in a cell from the subject comprising:
   (a) performing isoform-specific qRT-PCR of the full-length MTHFR encoding mRNA using a first primer consisting of SEQ ID NO 5 and a second primer consisting of SEQ ID NO 6,
   (b) performing isoform-specific qRT-PCR of the truncated MTHFR encoding mRNA using a third primer consisting of SEQ ID NO 7 and a fourth primer consisting of SEQ ID NO 8,
   c) calculating a Li/Si score using the Ct values generated in steps (a) and (b);
   discontinuing a treatment comprising one or more of methotrexate, azathioprine, chloroquine, or naltrexone;
   administering a treatment comprising one or more anti-inflammatory drugs excluding methotrexate, azathioprine, chloroquine, or naltrexone;
   wherein the Li/Si score is between a threshold value of 0.65 and 2.0.

3. The method of claim 2, wherein the inflammatory disorder is selected from the group consisting of rheumatoid arthritis and systemic lupus erythematosus.

4. The method of claim 2, wherein the inflammatory disorder is rheumatoid arthritis.

5. The method of claim 2, wherein the inflammatory disorder is systemic lupus erythematosus.

6. The method of claim 2, wherein the subject is a human subject.

7. The method of claim 2, wherein the anti-inflammatory drug is administered orally.

8. The method of claim 2, wherein the anti-inflammatory drug is selected from the group consisting of sulfasalazine or leflunomide.

* * * * *